United States Patent
Kwok et al.

(10) Patent No.: US 6,860,269 B2
(45) Date of Patent: *Mar. 1, 2005

(54) FOREHEAD SUPPORT FOR FACIAL MASK

(75) Inventors: Philip R. Kwok, Chatswood (AU); Michael K. Gunaratnam, Marsfield (AU); Perry D. Lithgow, Glenwood (AU); Jonathan P. Harrison, Redfern (AU); Jonathan L. Liston, Redfern (AU); Robert S. Matchett, Mosman (AU); Robert E. Styles, Glenhaven (AU)

(73) Assignee: Resmed Limited, North Ryde (AU)

( * ) Notice: Subject to any disclaimer, the term of this patent is extended or adjusted under 35 U.S.C. 154(b) by 182 days.

This patent is subject to a terminal disclaimer.

(21) Appl. No.: 10/264,326

(22) Filed: Oct. 4, 2002

(65) Prior Publication Data

US 2003/0034034 A1 Feb. 20, 2003

Related U.S. Application Data

(63) Continuation of application No. 09/502,745, filed on Feb. 11, 2000, now Pat. No. 6,532,961.

(30) Foreign Application Priority Data

Jun. 18, 1999 (AU) .............................................. PQ1040

(51) Int. Cl.$^7$ .............................................. A62B 18/08
(52) U.S. Cl. .............................. 128/207.11; 128/207.17; 128/207.18; 128/205.25
(58) Field of Search ........................ 128/206.24, 203.29, 128/204.11, 205.27, 206.12–207.18

(56) References Cited

U.S. PATENT DOCUMENTS

| | | |
|---|---|---|
| 781,516 A | 1/1905 | Guthrie |
| 812,706 A | 2/1906 | Warbasse |
| 1,081,745 A | 12/1913 | Johnston et al. |
| 1,192,186 A | 7/1916 | Greene |
| 1,653,572 A | 12/1927 | Jackson |
| 1,926,027 A | 9/1933 | Biggs |
| 2,123,353 A | 7/1938 | Catt |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,671 A | 5/1945 | Fink |
| 2,415,846 A | 2/1947 | Randall |
| 2,438,058 A | 3/1948 | Kincheloe |
| 2,578,621 A | 12/1951 | Yant |
| 2,590,006 A | 3/1952 | Gordon |
| 2,931,356 A | 4/1960 | Schwarz |
| D188,084 S | 5/1960 | Garelick |
| 2,939,458 A | 6/1960 | Lundquist |

(List continued on next page.)

FOREIGN PATENT DOCUMENTS

| | | |
|---|---|---|
| AU | 91/77110 B | 11/1991 |
| AU | 94/64816 B | 12/1994 |
| AU | 95/16178 B | 7/1995 |

(List continued on next page.)

OTHER PUBLICATIONS

Product Brochure for "Sullivan Mirage" Face Mask, ©1997, ResMed, 4 pages.

(List continued on next page.)

*Primary Examiner*—Glenn K. Dawson
(74) *Attorney, Agent, or Firm*—Nixon & Vanderhye P.C.

(57) ABSTRACT

A forehead support is adapted to be secured to a respiratory mask. The forehead support includes a joining member for securing to the mask and a cushion frame pivotally mounted to the joining member. The cushion frame is adapted to located one or more forehead cushions. The cushion frame is also selectively lockable at two or more predetermined angular positions relative to the joining member.

27 Claims, 8 Drawing Sheets

U.S. PATENT DOCUMENTS

| | | |
|---|---|---|
| 3,013,556 A | 12/1961 | Galleher |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,750,333 A | 8/1973 | Vance |
| 3,752,157 A | 8/1973 | Malmin |
| 3,796,216 A | 3/1974 | Schwarz |
| 3,799,164 A | 3/1974 | Rollins |
| D231,803 S | 6/1974 | Huddy |
| 3,830,230 A | 8/1974 | Chester |
| 4,077,404 A | 3/1978 | Elam |
| D250,131 S | 10/1978 | Lewis et al. |
| 4,120,302 A | 10/1978 | Ziegler |
| 4,167,185 A | 9/1979 | Lewis |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,328,797 A | 5/1982 | Rollins et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,467,799 A | 8/1984 | Steinberg |
| 4,522,639 A | 6/1985 | Ansite et al. |
| 4,558,710 A | 12/1985 | Eichler |
| 4,616,647 A | 10/1986 | McCreadie |
| 4,622,964 A | 11/1986 | Flynn |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A * | 4/1990 | Kopala et al. ......... 128/207.18 |
| 4,938,210 A | 7/1990 | Shene |
| 4,938,212 A | 7/1990 | Snook et al. |
| 4,944,310 A | 7/1990 | Sullivan |
| D310,431 S | 9/1990 | Bellm |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,069,205 A | 12/1991 | Urso |
| D323,908 S | 2/1992 | Hollister et al. |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| D334,633 S | 4/1993 | Rudolph |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,662,101 A | 9/1997 | Ogden et al. |
| 5,666,946 A | 9/1997 | Langenback |
| 5,685,296 A | 11/1997 | Zdrojkowski et al. |
| 5,687,715 A | 11/1997 | Landis et al. |
| 5,715,814 A | 2/1998 | Ebers |
| 5,746,201 A | 5/1998 | Kidd |
| 5,813,423 A | 9/1998 | Kirchgeorg |
| 5,832,918 A | 11/1998 | Pantino |

| | | | |
|---|---|---|---|
| 6,044,844 A | 4/2000 | Kwok et al. | |
| 6,119,693 A * | 9/2000 | Kwok et al. | 128/207.11 |
| 2003/0019496 A1 * | 1/2003 | Kopacko et al. | 128/206.24 |

FOREIGN PATENT DOCUMENTS

| | | |
|---|---|---|
| AU | A 32914/95 | 2/1996 |
| AU | 9459430 | 2/1996 |
| AU | A 41018/97 | 4/1998 |
| AU | A 89312/98 | 1/1999 |
| CA | 1039144 | 9/1928 |
| DE | 459 104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 | 4/1987 |
| DE | 3539073 A1 | 5/1987 |
| DE | 4004157 C1 | 4/1991 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 0427474 A2 | 5/1991 |
| EP | 0 462 701 A1 | 12/1991 |
| EP | 0 602 424 | 11/1993 |
| EP | 0 608 684 A1 | 8/1994 |
| EP | 0 0697 225 | 7/1995 |
| EP | 178 925 A2 | 4/1996 |
| EP | 0 747 078 A2 | 12/1996 |
| EP | 0 821 978 | 2/1998 |
| FR | 2 574 657 A1 | 6/1986 |
| FR | 2 658 725 A1 | 8/1991 |
| FR | 2 749 176 | 12/1997 |
| GB | 1395391 | 5/1975 |
| GB | 1 467 828 | 3/1977 |
| GB | 2145335 A | 3/1985 |
| GB | 2147506 A | 5/1985 |
| GB | 2 164 569 A | 3/1986 |
| GB | 2 186 801 | 8/1987 |
| GB | 2 267 648 A | 12/1993 |
| JP | 09/216240 A | 8/1997 |
| JP | 11-000397 | 1/1999 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |
| WO | WO 00/57942 | 10/2000 |

OTHER PUBLICATIONS

Product Brochure for "Sullivan Mirage" Face Mask, ©1998, ResMed, 4, pages.

Color Photo of "Weinmann Mask" 1998, 1 page.

"The ResMed Range of Mask Systems" product brochure, Nov. 1995, 4 pages.

"Somnotron CPAP–Gerat WM 2300" instruction manual, Weinmann Hamburg (1991), 11 pages.

9 photographs of Weinmann mask, WM 23122, 1991.

Mask 1 Photographs, Respironics Inc., Reusable Full Mask (small) Part #452033 Lot #951108.

Mask 2 Photographs, Puritan – Bennett, Adam Curcuit, Shell Part #231700, Swivel Part #616329–00, Pillows (medium) Part #616324.

Mask 3 Photographs, DeVilbiss Healthcare Inc., Devilbiss Seal–Ring and CPAP Mask Kit (medium), Part #73510–669.

Mask 4 Photographs, Respironics Inc., Monarch Mini Mask with Pressure Port. Part #572004, Monarch Headgear, Part #572011.

Mask 5 Photographs, Healthdyne Technologies, Nasal CPAP Mask (medium narrow), Part #702510.

Mask 6 Photographs, Healthdyne Technologies, Soft Series Nasal CPAP Mask, Part #702020.

Mask 7 Photographs, DeVilbiss Healthcare Inc., Small Mask and Seal Rings, Part #73510–668.

Mask 8 Photographs, Respironics Inc., Reusable Contour Mask (medium), Part #302180.

Mask 9 Photographs, Healthdyne Technologies, Healthdyne Large Headgear.

Mask 10 Photographs, Respironics Inc., Soft Cap (medium), Part #302142.

Mask 11 Photographs, Weinmann: Hamburg, Nasalmaskensystem mit Schalldämpfer (medium), Part #WN 23105.

Mask 12 Photographs, Life Care.

Mask 13 Photographs, Healthdyne Technologies.

Mask 14 Photographs, King System.

Mask 15 Photographs, Respironics Inc., Pediatric Mask.

Mask 16 Photographs, Hans Rudolph Inc., Han Rudolph Silicone Rubber Face Mask/8900.

* cited by examiner

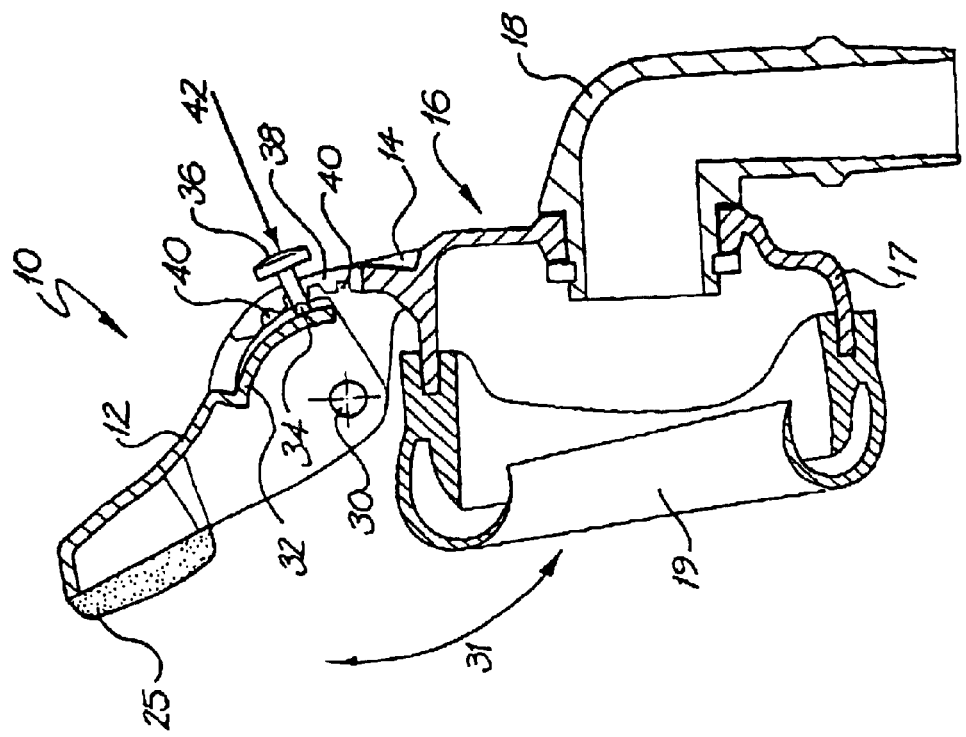
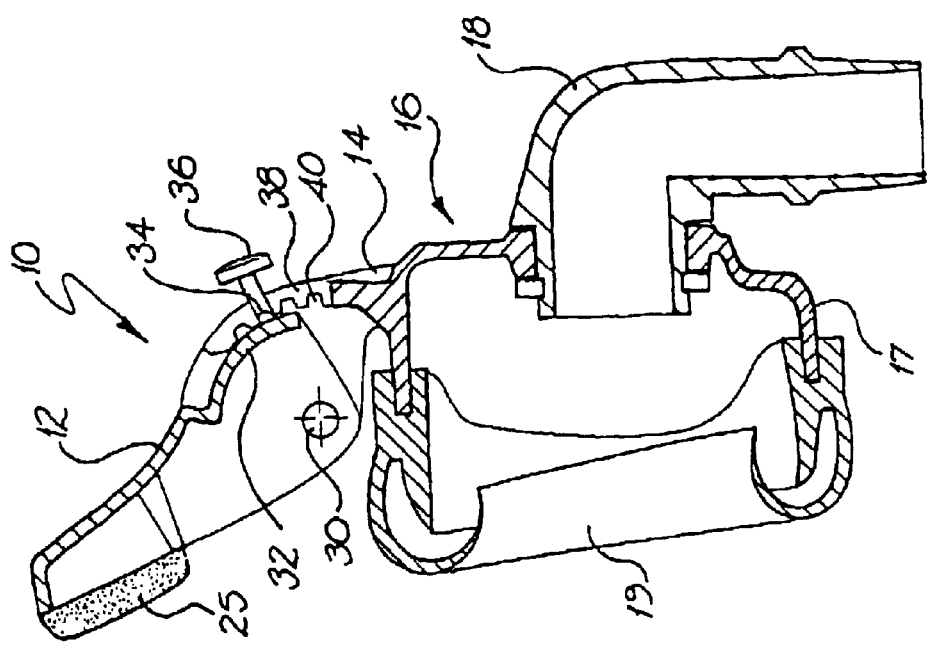

FOREHEAD SUPPORT FOR FACIAL MASK

CROSS REFERENCE TO RELATED APPLICATION

This application is a continuation of U.S. application Ser. No. 09/502,745, filed Feb. 11, 2000, now U.S. Pat. No. 6,532,961, the specification and drawings of which are incorporated herein by reference.

FIELD OF THE INVENTION

The present invention relates to a forehead support for a facial mask used to supply breathable gas to a wearer's airways.

The invention has been developed primarily for use in supporting a nasal mask used in Continuous Positive Airway Pressure (CPAP) treatment of, for example, Obstructive Sleep Apnea (OSA) and other ventilatory assistance treatments such as Non-Invasive Positive Pressure Ventilation (NIPPV) and will be described hereinafter with reference to this application. However, it will be appreciated that the invention is not limited to these particular uses and is also suitable for use with, for example, full-face (ie. nose and mouth) masks.

BACKGROUND OF THE INVENTION

CPAP treatment is a common ameliorative treatment for breathing disorders including OSA. CPAP treatment, as described in U.S. Pat. No. 4,944,310, provides pressurised air or other breathable gas to the entrance of a patient's airways at a pressure elevated above atmospheric pressure, typically in the range 4–20 cm $H_2O$.

It is also known for the level of treatment pressure to vary during a period of treatment in accordance with patient need, that form of CPAP being known as automatically adjusting nasal CPAP treatment, as described in U.S. Pat. No. 5,245,995.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase of respiration.

In other NIPPV modes the pressure can be made to vary in a complex manner throughout the respiratory cycle. For example, the pressure at the mask during inspiration or expiration can be varied through the period of treatment, as disclosed in the applicant's international PCT patent application No. PCT/AU97/00631.

Typically, the ventilatory assistance for CPAP or NIPPV treatment is delivered to the patient by way of a nasal mask. Alternatively, a mouth mask or full face mask or nasal prongs can be used. In this specification any reference to a mask is to be understood as incorporating a reference to a nasal mask, mouth mask, full face mask or nasal prongs, unless otherwise specifically indicated.

In this specification any reference to CPAP treatment is to be understood as embracing all of the above described forms of ventilatory treatment or assistance.

A CPAP apparatus broadly comprises a flow generator constituted by a continuous source of air or other breathable gas such as a hospital piped supply or a blower. In the latter case, an electric motor drives the blower and is typically controlled by a servo-controller under the control of a microcontroller unit. In either case, the gas supply is connected to a conduit or tube which in turn is connected to a patient nasal or full-face mask which incorporates, or has in close proximity, an exhaust to atmosphere for venting exhaled gases. Examples of prior art nasal masks are shown in U.S. Pat. Nos. 4,782,832 and 5,243,971.

The supply conduit delivers gas into a chamber formed by walls of the mask. The mask includes a cushion positioned against the wearer's face and is normally secured to the wearer's head by straps. The straps are adjusted to pull the mask against the face to achieve a gas tight seal between the cushion and the wearer's face.

A problem that arises with existing masks is that with the use of straps, the mask is compressed against the wearer's face and may push unduly hard on the wearer's nose. Additionally, the mask may move around the wearer's face. Thus, there has been hitherto provided a forehead support, which provides a support mechanism between the mask and the forehead. This forehead support prevents both the mask from pushing too strongly against the wearer's nose and/or facial region as well as minimising movement of the mask with the addition of a contact point between the mask and the wearer's head thereby reducing uncomfortable pressure points. Additionally, the forehead support can be arranged to prevent the gas supply conduit from contacting the wearer's forehead or face.

Forehead supports with a single cushion and a single contact point on the forehead are known.

The applicant's U.S. patent application Ser. No. 09/008,708 relates to a substantially rigid one-piece forehead support having a pair of forehead cushions mounted at each outer end of the support. This forehead support is connected to the top of a facial mask and includes an adjustment mechanism to allow the spacing between the top of the facial mask and the forehead support to be altered between predetermined positions to alter the angle of the mask relative to the wearer's head to suit the wearer's facial topography.

The applicant's Australian provisional patent application No. PP9499 relates to a forehead support having a pair of pivotable arms that each have a forehead cushion mounted at their distal end. This forehead support is connected to the top of a mask and includes an adjustable mechanism to allow the angle between the arms to be altered between predetermined positions to alter the angle of the mask relative to the wearer's head to suit the wearer's facial topography.

It is an object of the present invention to provide an alternate form of forehead support.

SUMMARY OF THE INVENTION

Accordingly, in a first aspect, the present invention provides a forehead support adapted to be secured to a respiratory mask, said forehead support including a joining member for securing to the mask and a cushion frame pivotally mounted to the joining member, wherein: the cushion frame is adapted to locate one or more forehead cushions; the cushion frame is adapted to pivot relative to the joining member; and the cushion frame is selectively lockable at two or more predetermined angular positions relative to the joining member.

In a second aspect, the present invention provides a respiratory mask assembly comprising a respiratory mask and a forehead support adapted to be secured to the mask, said forehead support including a joining member for securing to the mask and a cushion frame pivotally mounted to the joining member, wherein: the cushion frame is adapted to locate one or more forehead cushions; the cushion frame is adapted to pivot relative to the joining member; and the cushion frame is selectively lockable at two or more predetermined angular positions relative to the joining member.

The cushion frame is preferably T-shaped and includes a forehead cushion at each end of the upper portion of the T.

Preferably, one of the cushion frame or joining member includes a tongue adapted to be received in one of at least two grooves provided on the other of the cushion frame or joining member so as to lock the cushion frame and joining member at one of the two or more predetermined angular positions.

More preferably, a pair of the tongues are provided on the cushion frame and at least two pairs of grooves are provided on the joining member.

The tongue(s) is/are preferably provided on a semi-rigid member which is adapted to permit the tongue(s) to be moved out of engagement with the grooves by manual manipulation of the member. The tongue(s) is/are preferably connected to a button adapted to protrude from the cushion frame to facilitate manual manipulation of the member.

The cushion frame preferably includes means to connect a head strap thereto.

The mask preferably also include means to connect a head strap thereto.

The joining member can be produced from, for example, polypropylene or polycarbonate.

The mask can include a mask shell and a mask cushion. The mask shell can be produced from, for example, polypropylene or polycarbonate.

The cushion frame can be produced from, for example, polypropylene or polycarbonate.

BRIEF DESCRIPTION OF THE DRAWINGS

Preferred embodiments of the invention will now be described, by way of examples only, with reference to the accompanying drawings in which:

FIG. 2 is a cross sectional side view of the forehead support shown in FIG. 1 with the tongue of the cushion frame engaged with one of the pairs of grooves of the joining member;

FIG. 3 is a cross sectional side view of the forehead support shown in FIG. 1 with the tongue of the cushion frame free of engagement with the pairs of grooves of the joining member;

DETAILED DESCRIPTION OF PREFERRED EMBODIMENTS

Figure 1:
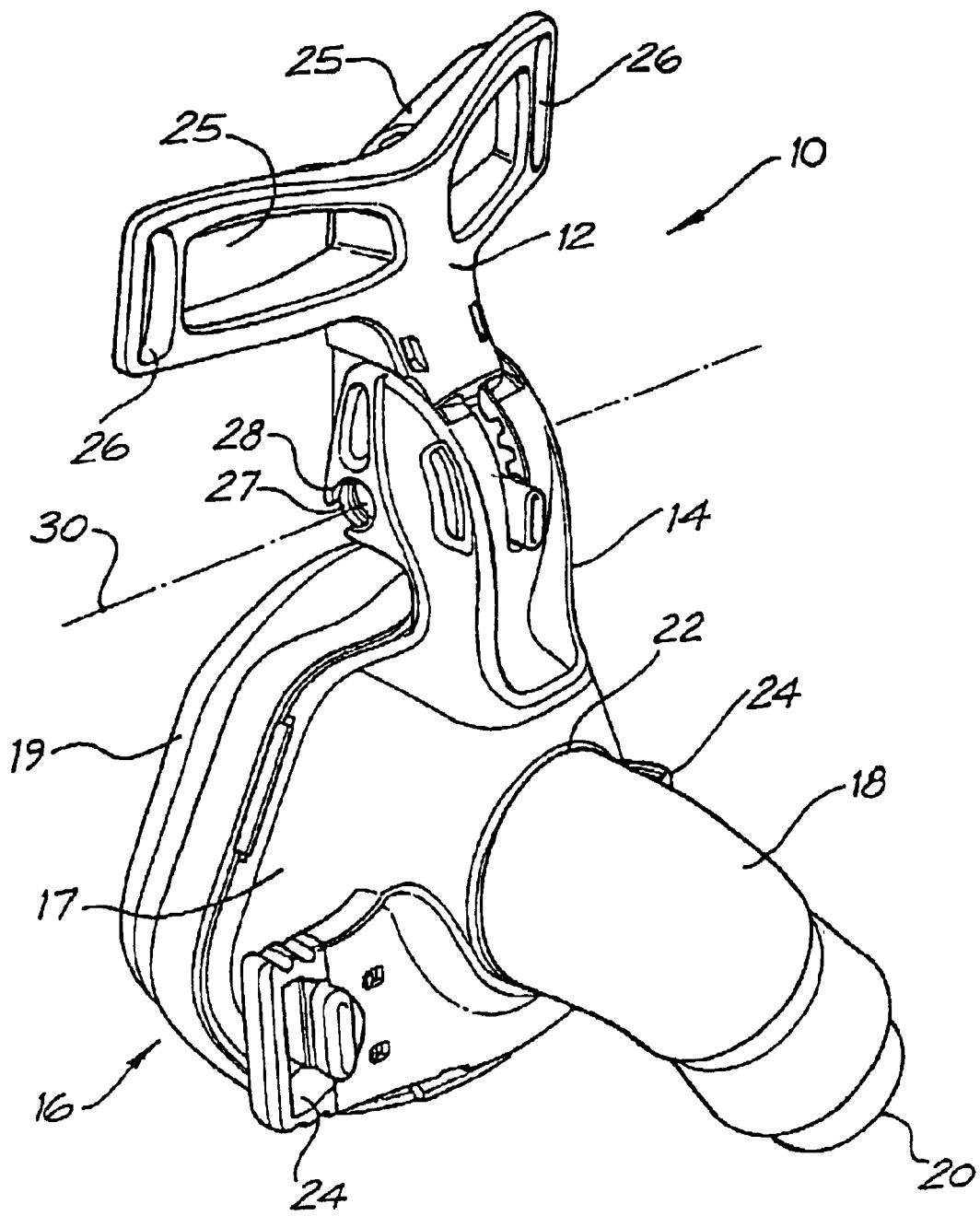
FIG. 1 is a front perspective view of a first embodiment of a forehead support according to the invention connected to a nasal mask.
Figure 4:
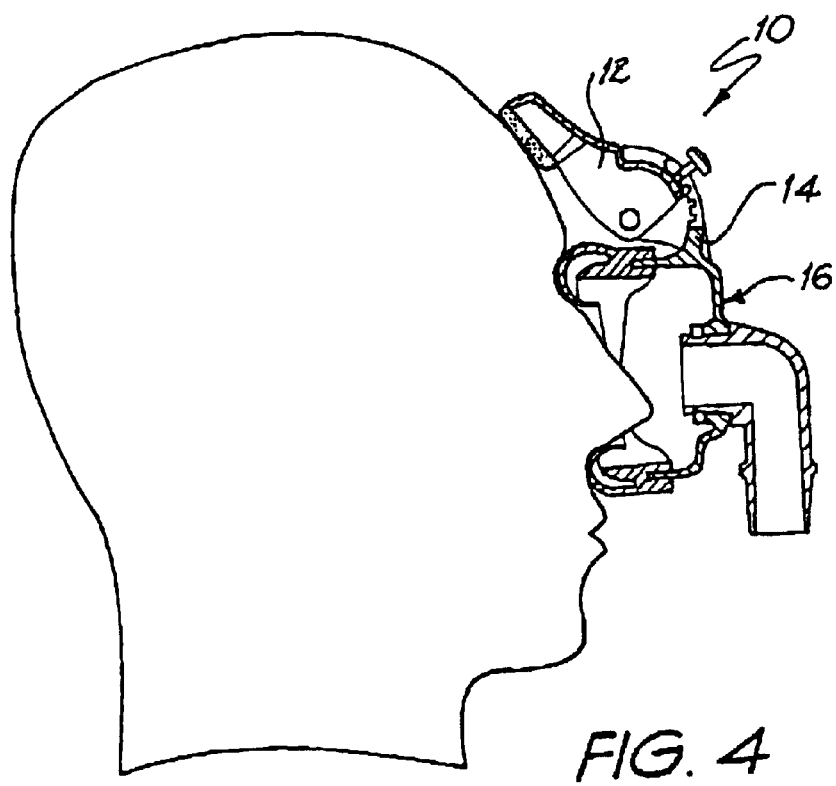
FIG. 4 is a cross sectional side view of the forehead support shown in FIG. 1 adjacent a wearer's head with the tongues and grooves engaged at the first of four positions.
Figure 5:
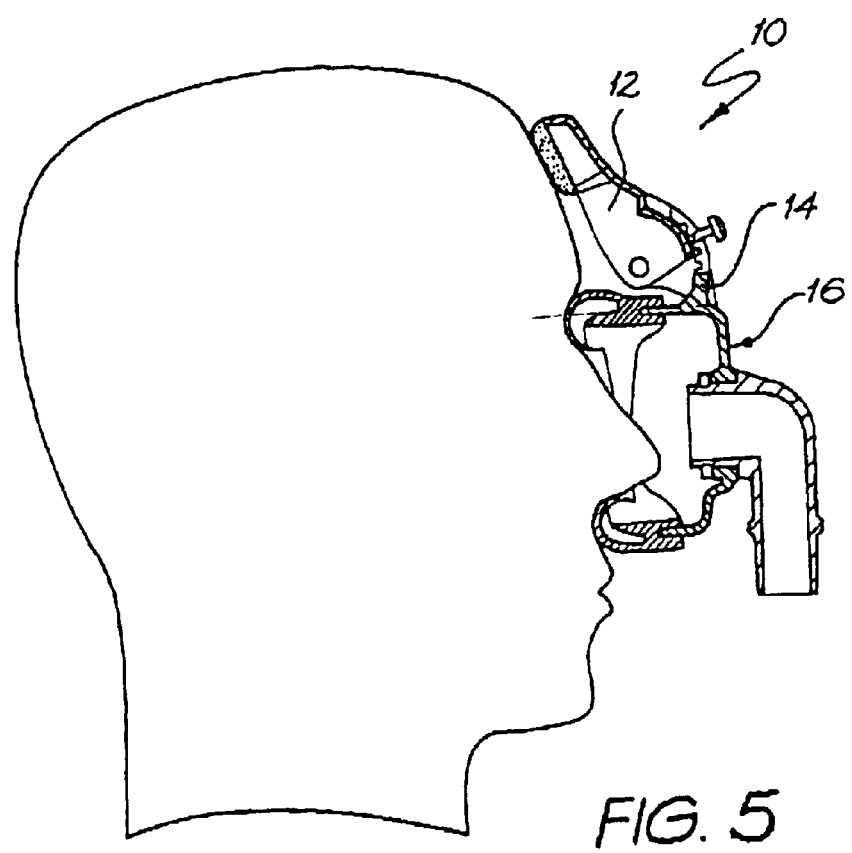
FIG. 5 is a cross sectional side view of the forehead support shown in FIG. 1 adjacent a wearer's head with the tongues and grooves engaged in the second of four positions.

FIG. 1 shows a first embodiment of a forehead support 10 according to the present invention. The forehead support 10 includes a generally T-shaped cushion frame 12 pivotally mounted to a joining member 14. The joining member 14 is connected to a nasal respiratory mask 16 used to supply breathable gas to a wearer's airways.

The mask 16 includes a mask shell 17 and a mask cushion 19. The mask shell 17 also includes an angled connector 18 which has a distal end 20 for connection to a gas supply conduit (not shown) and a proximal end 22 for connection to the mask 16. The connector 18 communicates the supplied gas from the gas supply conduit to the interior of the mask 16. The mask shell 17 also includes a pair of slotted connectors 24 to which are respectively connected ends of a lower head strap (not shown) for securing the nasal mask to the wearer's head.

The joining member 14 is connected on top of the mask shell 17 generally adjacent and above the wearer's nose. It will be appreciated that the nasal mask 16 shown is just one example of a respiratory mask that could be supported by the forehead support 10. For example, the forehead support also finds application in supporting full-face (ie. nose and mouth) masks.

Forehead supports according to the invention can also be used with facial masks in which the gas supply connector 18 is incorporated into the mask in the general position of the joining member 14. In this type of mask, the supplied gas flows through or past the forehead support 10.

The T-shaped cushion frame 12 includes a pair of forehead cushions 25 mounted at each end of the upper portion of the T on the wearer contacting side. Examples of cushions 25 include open or closed cell foam, silicone, dual durometer foams, single pads or multiple pads joined together. The forehead cushions 25 can be integrally moulded with the frame 12 or attached thereto by clips or adhesives or the like. The flame 12 also includes a slotted connector 26 adjacent each of the forehead cushions 25 to which are respectively connected ends of an upper head strap (not shown) for securing the cushion frame 12 to the wearer's head.

The T-shaped cushion frame 12 also includes a pair of shafts 27 (only one shown) on the lower portion of the T which are each respectively received in part circular openings 28 (only one shown) provided on the joining member 14. The shafts 27 can pivot or rotate in their respective openings 28 to provide for pivotal or rotational movement between the cushion frame 12 and the joining member 14 about axis 30 in the direction of double-headed arrow 31.

The curved shape of the cushions 25 allows them to effectively "roll" over the wearer's forehead during angular adjustment between the cushion frame 12 and the joining member 14.

As best shown in FIGS. 2 and 3, the cushion frame 12 also includes a flexible member 32 which has two side by side spaced apart tongues 34 and a middle protruding button 36 on its distal end. The joining member 14 also includes two generally arcuate shaped portions 38 that each have a pair of four grooves 40. It will be appreciated that the pair of four grooves is merely preferable and that only two or more grooves are required. It will also be appreciated that the flexible member 32 can be on the joining member 14 and the grooves 40 can be on the cushion frame 12. The tongue 34 and the grooves 40 extend in a direction substantially parallel to a line extending radially from the axis 30.

The cushion frame 12 is constructed from a plastics material, such as polypropylene or polycarbonate, which allows the member 32 to be flexed relative to the cushion frame 12 upon which is mounted when pressure is applied to the button 36 in the direction of arrow 42. The corresponding movement of the tongues 34 releases them from engagement with one of the pairs of grooves 40 (as shown in FIG. 3) to allow angular adjustment between the cushion frame 12 and the joining member 14 about the axis 30. Releasing the button 36 allows the tongue 34 to resiliently flex back towards the grooves 40. When the tongues 34 and one of the pairs of grooves 40 are aligned (as shown in FIGS. 2 and 4 to 7) the tongues 34 engage one of the pair of grooves 40. When the tongues 34 are engaged with one of the pair of grooves, the cushion frame 12 and joining member 14 are locked against pivotal movement therebetween at a predetermined angle.

FIGS. 4 to 7 respectively show forehead support 10 adjacent the heads of different wearers with the tongues 34 engaged in the first, second, third and fourth of the four pairs of grooves 40.

Figure 6:
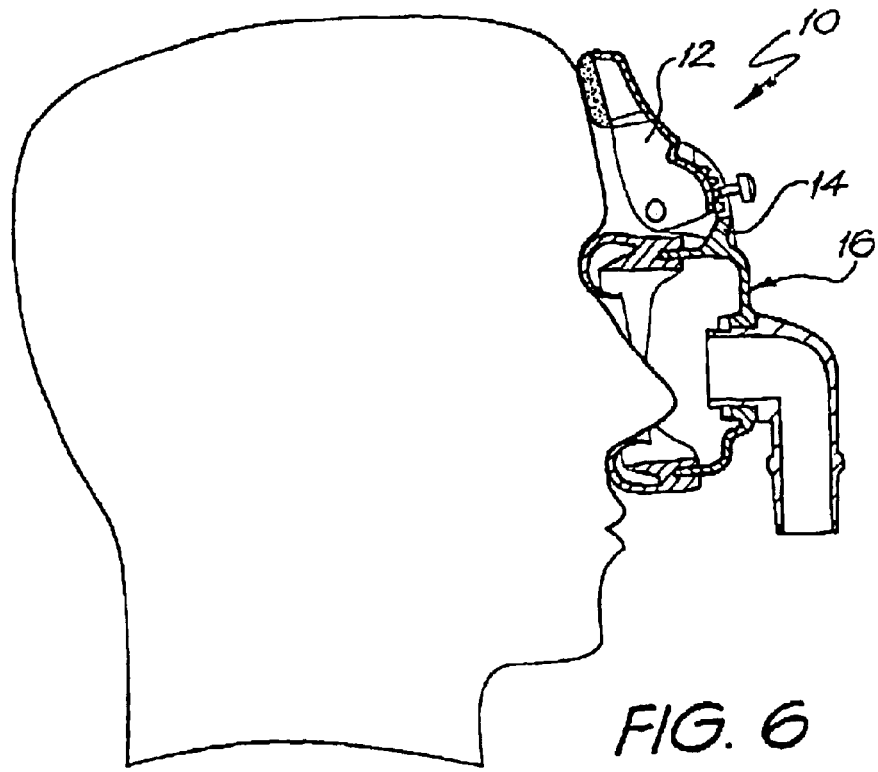
FIG. 6 is a cross sectional side view of the forehead support shown in FIG. 1 adjacent a wearer's head with the tongues and grooves engaged at the third of four positions.
Figure 7:
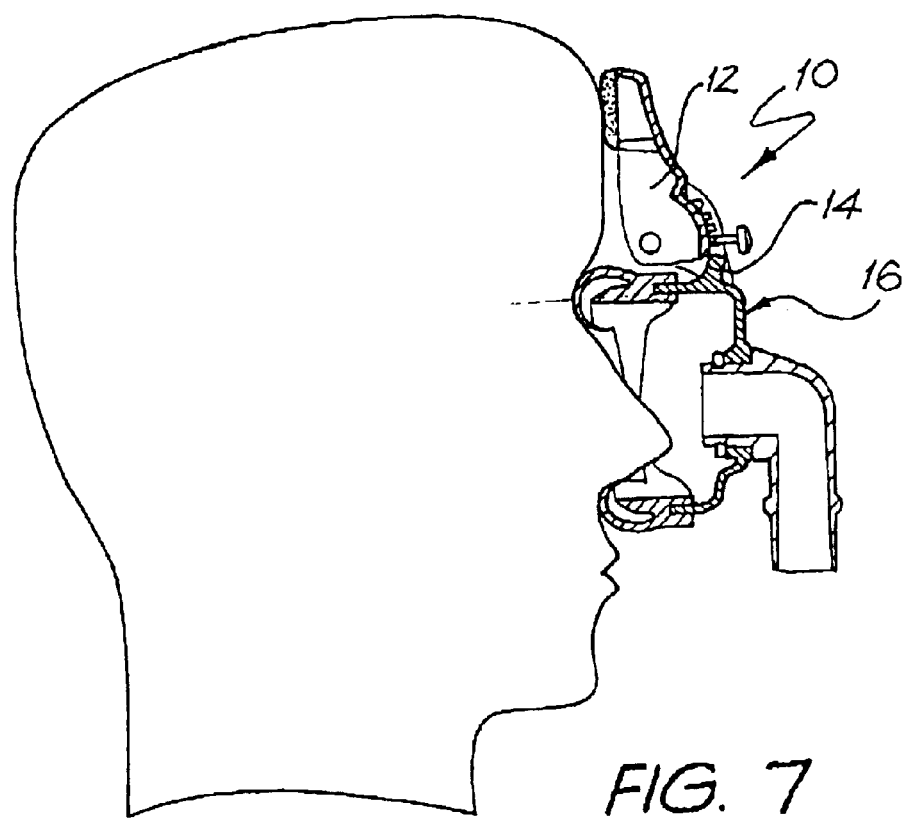
FIG. 7 is a cross sectional side view of the forehead support shown in FIG. 1 adjacent a wearer's head with the tongues and grooves engaged at the fourth of four positions.

As FIGS. 4 to 7 show, the angle between the cushion frame 12 and the joining member 14 adjacent the wearer's forehead can be increased to suit wearer's with relatively high nasal regions and relatively low foreheads (FIGS. 4 and 5) and decreased to suit wearers with relatively low nasal regions and relatively high foreheads (FIGS. 6 and 7).

Figure 8:
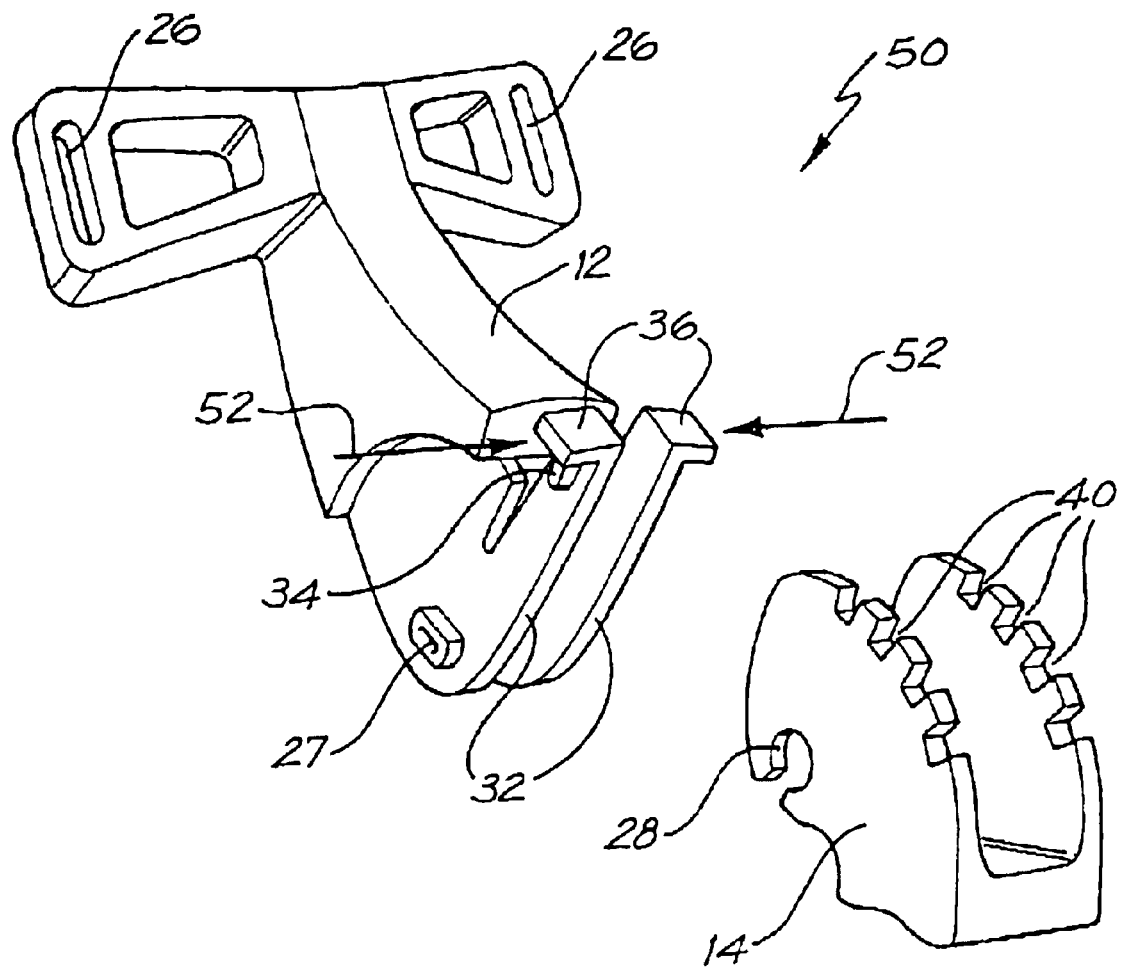
FIG. 8 is a partial exploded perspective view of a second embodiment of a forehead support according to the invention.
Figure 11:
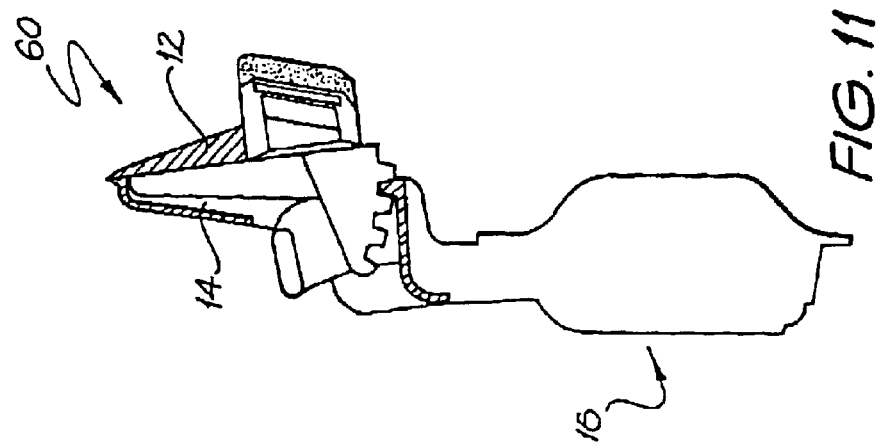
FIG. 11 is a cross sectional view of the forehead support shown in FIG. 9 with the tongue and grooves engaged at the second of four positions.
Figure 10:
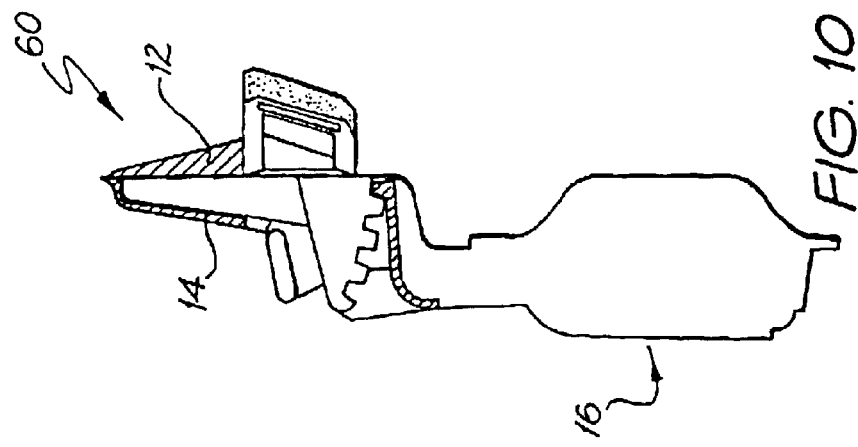
FIG. 10 is a cross sectional view of the forehead support shown in FIG. 9 with the tongue and grooves engaged at the first of four positions.

In this way the forehead support 10 advantageously allows the mask 16 to be positioned to comfortably suit the particular topography of the wearer's face to ensure the mask cushion 19 is positioned ideally relative to the wearer's face. As examples, the relative position of the cushion frame 12 and the joining member 14 in FIG. 4 would be more suitable for use with a wearer having a shallow forehead or protruding cheeks or nose whilst the position of the cushion frame and joining member 14 in FIG. 7 would be more suitable for use with a wearers having a protruding or bulbous forehead. FIG. 8 shows a second embodiment of a forehead support 50 according to the present invention. Like reference numerals to those used in describing the first embodiment will be used to denote like features in relation to the second embodiment.

In the second embodiment, their are two buttons 36. Pressing the buttons together in the direction of arrows 52 flexes the tongues 34 towards each other to disengage them from the grooves 40 and allow angular adjustment between the cushion frame 12 and the joining member 14. Releasing the buttons 36 allows the tongues 34 to resiliently flex towards, and into engagement with, the grooves 40 to lock the cushion frame 12 and the joining member 14 against relative pivotal movement.

FIGS. 9 to 14 show a third embodiment of a forehead support 60 according to the present invention. Like reference to those used in describing the first embodiment will also be used to denote like features in relation to the third embodiment.

Figure 9:
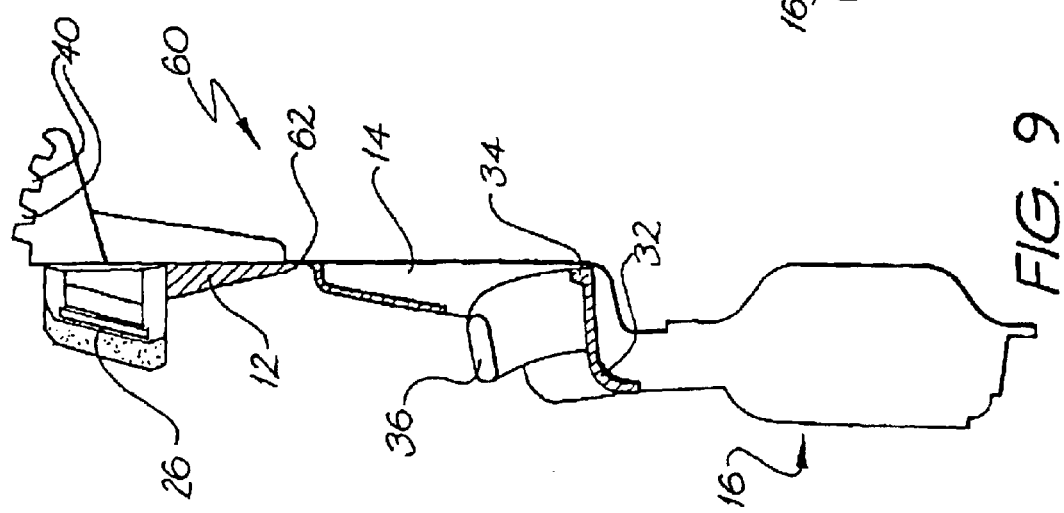
FIG. 9 is a cross sectional side view of a third embodiment of a forehead support according to the invention that includes an integrally formed cushion frame and joining member.
Figure 14:
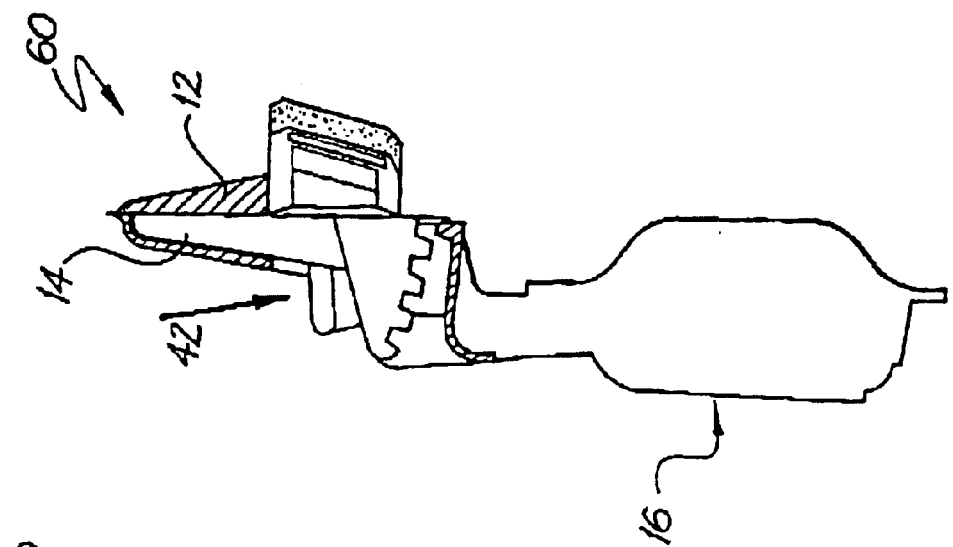
FIG. 14 is a cross sectional view of the forehead support shown in FIG. 9 with the tongue free of engagement with the grooves.
Figure 13:
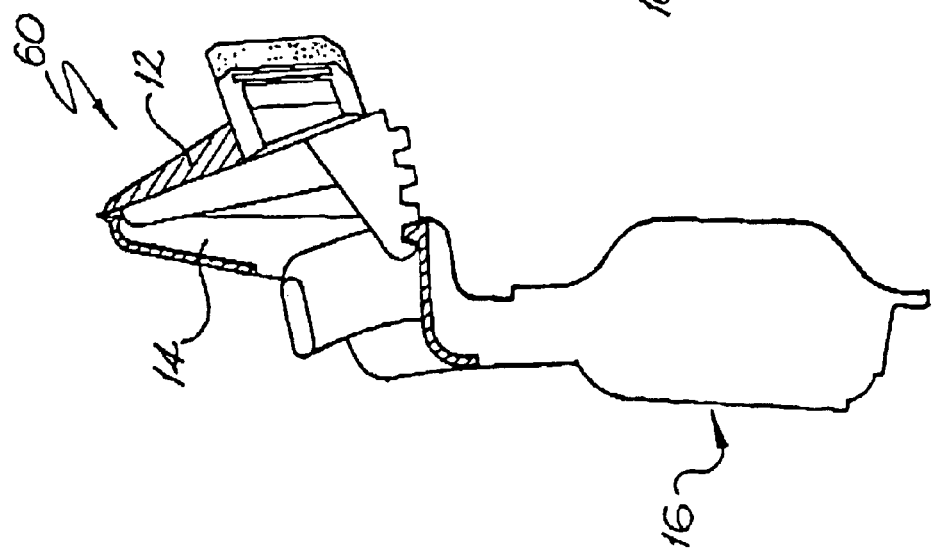
FIG. 13 is a cross sectional view of the forehead support shown in FIG. 9 with the tongue and grooves engaged at the fourth of four positions.
Figure 12:
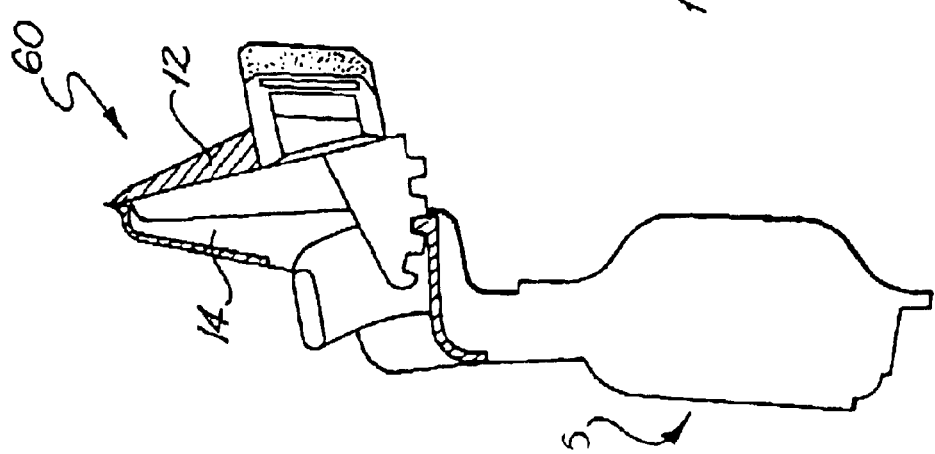
FIG. 12 is a cross sectional view of the forehead support shown in FIG. 9 with the tongue and grooves engaged at the third of four positions.

In the third embodiment, the cushion frame 12 is integrally moulded with the joining member 14 and joined by an integral hinge 62 (sometimes known as a natural or living hinge). The cushion frame 12 and the joining member 14 can be pivotted relative to each other about the hinge 62. The forehead support 60 is moulded in a substantially 'flat' configuration, as shown in FIG. 9. The cushion frame 12 is then pivotted through approximately 180° relative to the joining member 14 until the tongue 34 engages one of the four grooves 40. As with the earlier embodiments, pressing the button 36 in the direction of arrow 42 frees the tongue 34 from engagement with the grooves to allow adjustment of the angle between the cushion frame 12 and the joining member 14. The button 36 and the tongue 34 are inherently biased to a position engaging one of the grooves 40, again consistent with earlier embodiments.

In the preferred form shown, the mask shell 17 is also integrally formed with the joining member 14. This simplifies manufacturing and assembly and reduces production costs. The forehead support 60 is preferably manufactured from polypropylene due to its ability to mould integral hinges.

Figure 15:
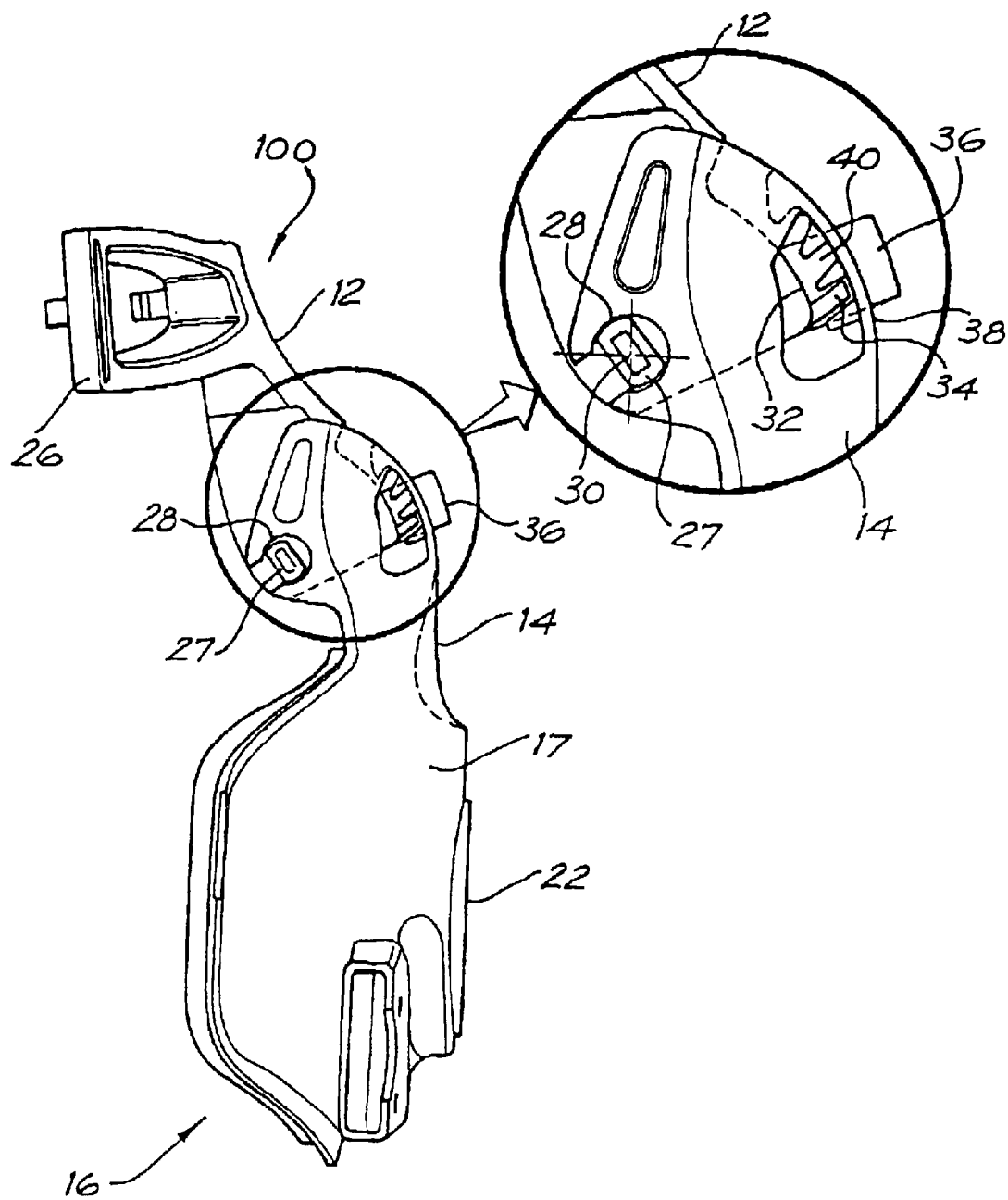
FIG. 15 is a side view, with enlarged details (in FIG. 16) of a fourth embodiment of a forehead support according to the invention.

FIGS. 15 and 16 show a fourth embodiment of a forehead support 100 according to the invention. Like reference to those used in describing the first embodiment will also be used to denote like features in relation to the fourth embodiment.

The fourth embodiment is almost identical to the first embodiment except the tongue 34 and the grooves 40 are angled with respect to a line extending radially from the axis 30 to the tongue 34 or the grooves 40. This angled arrangement reduces the likelihood that the tongue 34 will inadvertently release from engagement with one of the grooves 40 if the front of the mask 16 is subjected to a force in the direction of the wearer's face.

Although the invention has been described with reference to a specific example, it will be appreciated by those skilled in the art that the invention may be embodied in many other forms.

As an example, the forehead support can include means to resiliently bias the cushion frame and the joining member relative to one another such that they increase or decrease their angle relative to one another when the tongues are disengaged from one of the pairs of slots.

We claim:

1. A respiratory mask assembly including a respiratory mask and a forehead support adapted to be secured to the mask, said forehead support including a joining member for securing to the mask and a cushion frame adjustably mounted to the joining member, wherein:

the cushion frame is adapted to locate at least one forehead cushion made of foam, the cushion frame is adapted to move relative to the joining member, the cushion frame is selectively lockable at two or more predetermined positions relative to the joining member, the cushion frame includes a tongue adapted to be received in one of at least two grooves provided on the joining member so as to lock the cushion frame and joining member at one of the two or more predetermined positions, the cushion frame includes a slotted head strap connector portion at each lateral end of the cushion frame, the mask includes a mask shell and a mask cushion, and the joining member, the cushion frame and the mask shell are produced from polypropylene or polycarbonate.

2. The respiratory mask assembly as claimed in claim 1, wherein the cushion frame is a T-shaped frame and includes at least two opposed pivot pins running substantially parallel to a cross portion of the T-shaped frame.

3. The respiratory mask assembly as claimed in claim 1, wherein the cushion frame pivots relative to the joining member.

4. The respiratory mask assembly as claimed in claim 1, wherein the joining member is integrally formed with the mask.

5. A forehead support adapted to be secured to a respiratory mask, said forehead support including:

a joining member for securing to the mask; and a cushion frame adjustably mounted to the joining member, wherein:

the cushion frame is adapted to locate at least one forehead cushion, the cushion frame is adapted, in use, to move relative to the joining member along a predetermined path generally towards and away from the patient's forehead, the cushion frame includes a first finger-operated adjustment control member extending laterally outwards from a first lateral side of the cushion frame and a second finger-operated adjustment control member extending laterally outwards from a second lateral side of the cushion frame, and the first and second finger-operated adjustment control members are movable from a first position in which the cushion frame is unlocked and therefore adjustable along the predetermined path, to one of at least three predetermined locked positions relative to the joining member, the first and second finger-operated adjustment control members being spring-biased so as to selectively maintain the cushion frame in each of the at least three predetermined locked positions.

6. The support as claimed in claim 5, wherein the cushion frame includes a tongue adapted to be received in one of at least three grooves provided on the joining member so as to lock the cushion frame and joining member in one of the at least three predetermined locked positions.

7. The support as claimed in claim 5, wherein the cushion frame includes a slotted head strap connector portion at each end of the cushion frame.

8. A respiratory mask assembly comprising a respiratory mask provided with the forehead support set forth in claim 5, wherein the mask includes a shell provided with a nasal cushion, the joining member being integrally formed with the shell.

9. The mask assembly as claimed in claim 8, wherein the joining member is formed integrally with the mask.

10. A forehead support adapted to be secured to a respiratory mask, said forehead support comprising:

a joining member configured to be secured to the mask;

a generally T-shaped cushion frame adjustably mounted to the joining member to move relative to the joining member and generally towards and away from the patient's forehead along a generally curved path in use; and at least one foam cushion mounted on the cushion frame, wherein a cross portion of the generally T-shaped cushion frame is substantially transverse to the path along which the cushion frame moves, each lateral end of the cross of the T-shaped cushion frame includes a slotted connector portion adapted to receive a head strap, and the cushion frame is selectively lockable in at least two positions relative to the joining member, in use, while maintaining a generally operative orientation of the cushion frame relative to the patient.

11. The support as claimed in claim 10, further comprising at least one shaft coincident with an axis about which the cushion frame moves.

12. The support as claimed in claim 11, wherein the at least one shaft is integrally formed on the cushion frame.

13. The support as claimed in claim 11, wherein the at least one shaft includes two shafts provided on opposite sides of the cushion frame.

14. A respiratory mask assembly comprising a respiratory mask provided with the forehead support set forth in claim 10, wherein the mask is a nasal mask including a nasal cushion.

15. A respiratory mask assembly comprising:

a respiratory mask;

a forehead support secured to the mask via a joining member, said forehead support including a cushion frame mounted to the joining member so as to be movable relative to the mask when the cushion frame is secured to the mask; and at least one cushion mounted on the cushion frame, wherein:

the cushion frame is lockable in at least four predetermined locked positions relative to the patient's forehead, the mask includes a passage through which pressurized breathable gas is supplied via a swivel elbow, the joining member is integral with the mask, the cushion frame and the joining member include at least one pin and slot assembly by which, at least in part, the cushion frame may move, the cushion frame is generally T-shaped, and a cross portion of the T-shaped frame is substantially parallel to the pin, the cushion frame includes at least one tongue adapted to be received in one of at least four grooves provided on the joining member so as to lock the cushion frame and joining member in one of the at least four predetermined positions, said tongue is provided on a spring-biased member which is adapted to permit said tongue to be moved out of engagement with a respective one of the grooves by manual manipulation of the member, each end of the cushion frame includes a slotted head strap connector, and the mask includes a mask shell and a mask cushion.

16. A forehead support adapted to be secured to a respiratory mask for a wearer, said forehead support including:

a joining member for securing to the mask;

an adjustable frame adjustably mounted to the joining member;

a tongue and groove arrangement including a tongue and at least three grooves so that the adjustable frame is selectively lockable at three or more predetermined positions relative to the joining member, and a finger operated push button to manually adjust positioning of the tongue relative to the at least three grooves, wherein:

the push button and the tongue are supported by a common resilient member, the adjustable frame includes a foam pad member oriented towards the wearer in use, the adjustable frame includes at least one slotted head strap receiving portion, and the joining member and the adjustable frame are produced from polypropylene or polycarbonate.

17. The forehead support as claimed in claim 16, wherein the adjustable frame pivots or rotates relative to the joining member.

18. A respiratory mask assembly for a wearer, comprising:

a respiratory mask; and a forehead support secured to the mask via a joining member, said forehead support including an adjustable frame mounted to the joining member so as to be movable relative to the mask when the frame is secured to the mask, wherein the frame is lockable in at least four predetermined locked positions relative to the wearer's forehead via a tongue and groove arrangement including at least one tongue adapted to be received in one of at least four grooves so as to lock the frame and joining member in one of the at least four predetermined positions, the mask includes a passage through which pressurized breathable gas is supplied via a swivel elbow, the joining member is integrally formed with the mask, said tongue is provided on a spring-biased member which is adapted to permit said tongue to be moved out of engagement with a respective one of the grooves by manual manipulation of the member, the member is associated with a push button, the frame includes at least one slotted head strap receiving portion, and the mask includes a mask shell and a mask cushion.

19. A forehead support adapted to be secured to a respiratory mask of a wearer, said forehead support including a joining member for securing to the mask and an adjustable frame adjustably mounted to the joining member, wherein: the adjustable frame is adapted to locate a foam padded member to confront the wearer's forehead in use; the adjustable frame is adapted to move relative to the joining member along a curved path when the adjustable frame is secured to the mask; and the adjustable frame includes a depressable push button structured and configured to selectively lock the adjustable frame along said curved path in at least three predetermined angular positions relative to the joining member.

20. The support as claimed in claim 19, wherein the adjustable frame and joining member include a tongue and groove arrangement including at least one tongue adapted to be received in one of at least four grooves so as to lock the adjustable frame and joining member in one of the at least three predetermined angular positions.

21. The support as claimed in claim 20, wherein said at least one tongue is provided on a semi-rigid member which is adapted to permit said tongue to be moved out of engagement with a respective one of the grooves by manual manipulation of the semi-rigid member.

22. The support as claimed in claim 21, wherein said member is associated with a push button adapted to protrude from the adjustable frame to facilitate manual manipulation of the member.

23. The support as claimed in claim 19, wherein the adjustable frame pivots or rotates relative to the joining member during movement along the curved path.

24. The support as claimed in claim 23, wherein the adjustable frame cannot pivot or rotate beyond a predetermined maximum angular position in at least one direction.

25. The support as claimed in claim 24, wherein the adjustable frame cannot pivot or rotate beyond predetermined angular positions in each direction.

26. The support as claimed in claim in claim 19, wherein the adjustable frame and the joining member are produced from polypropylene or polycarbonate.

27. A respiratory mask assembly comprising:

a respiratory mask; and a forehead support secured to the mask via a joining member, said forehead support including an adjustable frame mounted to the joining member so as to be movable relative to the mask when the adjustable frame is secured to the mask, wherein:

the adjustable frame is lockable in at least two predetermined positions, the mask includes a front swivel elbow through which breathable gas is supplied, the joining member is formed integrally with the mask, the cushion frame and the joining member include a tongue-and-groove arrangement including a pair of adjacent tongues adapted to be received in one of at least two pairs of adjacent grooves so as to lock the adjustable frame and joining member at one of the at least two predetermined positions, each said tongue is provided on a flexible member which is adapted to permit each said tongue to be moved out of engagement with a respective one of the grooves by manual manipulation of the member, the tongues are associated with a common button adapted to facilitate manual manipulation of the member, the button is positioned on the member, and the nasal mask includes a mask shell and a nasal mask cushion.

* * * * *